US010457696B2

United States Patent
Fritz-Langhals

(10) Patent No.: US 10,457,696 B2
(45) Date of Patent: Oct. 29, 2019

(54) CATIONIC SILICON (II) COMPOUNDS AND METHOD FOR THE PRODUCTION THEREOF

(71) Applicant: WACKER CHEMIE AG, Munich (DE)

(72) Inventor: Elke Fritz-Langhals, Ottobrunn (DE)

(73) Assignee: WACKER CHEMIE AG, München (DE)

( * ) Notice: Subject to any disclaimer, the term of this patent is extended or adjusted under 35 U.S.C. 154(b) by 0 days.

(21) Appl. No.: 16/098,274

(22) PCT Filed: May 11, 2016

(86) PCT No.: PCT/EP2016/060531
§ 371 (c)(1),
(2) Date: Nov. 1, 2018

(87) PCT Pub. No.: WO2017/194100
PCT Pub. Date: Nov. 16, 2017

(65) Prior Publication Data
US 2019/0152999 A1    May 23, 2019

(51) Int. Cl.
*C07F 7/08*    (2006.01)
*C07F 17/00*    (2006.01)
*B01J 31/22*    (2006.01)

(52) U.S. Cl.
CPC ............ *C07F 7/0803* (2013.01); *C07F 17/00* (2013.01); *B01J 31/2295* (2013.01)

(58) Field of Classification Search
None
See application file for complete search history.

(56) References Cited

PUBLICATIONS

Holtmann et al., Organometallics 1999, 18, 5531-5538. (Year: 1999).*
Leszczynska et al.: "The Pentamethylcyclopentadienylsilicon(II) Cation as a Catalyst for the Specific Degradation of Oligo(ethyleneglycol) Diethers" Silicon (II) Compounds, Angew. Chem. 2011, 123, pp. 6975-6978.
Peter Jutzi: "The Pentamethylcyclopentadienylsilicon(II) Cation: Synthesis, Characterization, and Reactivity" Silicon Chemistry, Chemistry A European Journal, 2014, 20, pp. 9192-9207.
Jutzi et al.: "Synthesis, Crystal Structure, and Application of the Oxonium Acid . . . " Organometallics 2000, 19, pp. 1442-1444.
Jutzi et al.: "The (Me5C5)Si+ Cation: A Stable Derivative of HSi+", Science, vol. 305, Aug. 6, 2004, pp. 849-851.
Jutzi et al.: "Chemistry of decamethylsilicocene: oxidative addition of compounds with X—H bonds (X=F, Cl, Br, O, S)", Journal of Organometallic Chemistry 446, (1993), pp. 139-147.
Udo Holtmann et al.: "Reaction of Decamethylsilicocene with Group 13 Element Halides: Insertions, Rearrangements, and Eliminations", Organometallics 1999, vol. 18, No. 26, pp. 5531-5538.

* cited by examiner

*Primary Examiner* — Clinton A Brooks
*Assistant Examiner* — Kofi Adzamli

(57) ABSTRACT

The invention relates to a method for producing cationic silicon (II) compounds of general formula I $(R^aSi)^+HA^-$    (I)

by reacting the silicon (II) compounds of general formula II $(R^b{-}H)(R^aSi)^+$    (II)

with a hydride acceptor compound A,
wherein $R^a$, $(R^b{-}H)$ and A have the definitions described in claim 1;
to the cationic silicon (II) compounds of general formula I and use thereof as catalysts.

6 Claims, No Drawings

CATIONIC SILICON (II) COMPOUNDS AND METHOD FOR THE PRODUCTION THEREOF

CROSS-REFERENCE TO RELATED APPLICATIONS

This application is a U.S. National Phase Application of PCT/EP2016/060531, filed May 11, 2016, the contents of which are incorporated herein by reference in their entireties for all purposes.

FIELD OF THE INVENTION

The invention relates to cationic Si (II) compounds and a method for the production thereof and also use thereof as catalysts.

BACKGROUND OF THE INVENTION

Cationic silicon (II) compounds are highly reactive compounds, which are of industrial interest owing to their electronic structure, especially for catalytic purposes. It could be shown, for example in Angew. Chem. 2011, 123, 6975, that the cationic Si (II) compound $(C_5Me_5)Si^+B(C_6F_5)_4^-$ catalyses the conversion of ethers with high selectivity.

In particular, the lack of synthetic accessibility has long stood in the way of the use of this compound class. The compound $(C_5Me_5)Si^+B(C_6F_5)_4^-$ can be prepared from silicocene, $(C_5Me_5)_2Si$, —as described in Chem. Eur. Joc. 2014, 20, 9192—for example exclusively by reacting silicocene with the specific protic acid $(C_5H_2Me_5)^+B(C_6F_5)_4^-$, which is accessible only in a very complex, in part safety-critical 7-stage low temperature synthesis according to Organometallics 2000, 19, 1442 in connection with Science, 2004, 305, 849. Protic acids that are easier to access always result, as stated in J. Organomet. Chem. 1993, 446, 139, in oxidative addition with formation of an adduct with tetravalent silicon.

Thus, there is a need for a simpler method by which cationic silicon (II) compounds can be made accessible.

SUMMARY OF THE INVENTION

The invention relates to a method for producing cationic silicon (II) compounds of general formula I $(R^aSi)^+HA^-$     (I)

by reacting the silicon (II) compounds of general, formula II $(R^b\text{–}H)(R^aSi)^+$     (II)

with a compound A,
where
$R^a$ is a carbon-containing radical, which may additionally comprise heteroatoms such as nitrogen, oxygen or sulfur, bound to the cationic silicon atom via a covalent bond, ionic bond or via one or more π bonds with the cationic silicon atom,
$(R^b\text{–}H)$ is a π-bonded singly negatively charged radical of general formula III,

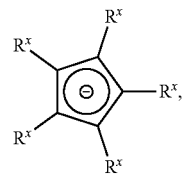

$R^x$ are monovalent or polyvalent organic radicals, which may also be bonded to one another to form a fused ring, with the proviso that at least one of the radicals $R^x$ is an organic radical bonded via carbon bearing at least one hydrogen atom, preferably in the alpha position to the ring, and
A is a compound which, as an electrophile, is capable of accepting electron pairs.

DETAILED DESCRIPTION OF PREFERRED EMBODIMENTS

It has been found that, surprisingly, cationic silicon (II) compounds can be prepared by transferring a negatively charged hydrogen atom, a hydride ion, to a hydride acceptor. Hydride acceptors are very readily accessible synthetically. In this manner, therefore, the accessibility of the cationic silicon (II) compounds is substantially simplified. A further advantage is that the reaction takes place at ambient temperature in high yield without forming by-products.

An example of the reaction that takes place in the method is elucidated by using a preferred cyclopentadienyl radical $(R^b\text{–}H)$ of general formula III, namely $(Cp\text{-}CHR^1R^2)^-$.

In the method, a hydride ion is transferred to the hydride acceptor A forming $HA^-$ and the compound $Cp=CR^1R^2$ (corresponds to $R^b$) according to reaction equation 1, $(Cp\text{-}CHR^1R^2)^-(R^aSi)^+ + A => Cp=CR^1R^2 + (R^aSi)^+ + HA^-$     (1), where Cp is a cyclopentadienyl radical.

The compound $HA^-$ that is also formed in the reaction forms the counterion to the cationic silicon (II) compound $(R^aSi)^+$.

The radical $R^a$ is preferably π-bonded and comprises at least two conjugated carbon-carbon double bonds.
$R^a$ is especially preferably a π-bonded cyclopentadienyl radical substituted by the radicals $R^y$ ($R^y{}_5Cp$) where
$R^y$ are monovalent or polyvalent organic radicals, which may be bonded also to one another to form fused rings.

In this case, the compound of general formula I has the structure of general formula Ia:

The radicals $R^a$ and $R^b$ may also be bonded to each other, preferably via one or more carbon radicals.

The radicals $R^y$ are preferably each independently hydrogen, linear or branched, acyclic or cyclic, saturated or mono- or polyunsaturated C1-C20 alkyl or C6-C20 aryl, particularly preferably C1-C3 alkyl, especially preferably methyl radicals. Example of radicals $R^y$ are alkyl radicals such as the methyl, ethyl, n-propyl, isopropyl, n-butyl, sec-butyl, isobutyl, tert-butyl, n-pentyl, sec-pentyl, isopentyl, neopentyl or tert-pentyl radical; hexyl radicals such as the n-hexyl radical; heptyl radicals such as the n-heptyl radical; octyl radicals such as the n-octyl radical, and isooctyl radicals such as the 2,4,4-trimethylpentyl radical; nonyl radicals such as the n-nonyl radical; decyl radicals such as the n-decyl radical; dodecyl radicals such as the n-dodecyl radical; hexadecyl radicals such as the n-hexadecyl radical; octadecyl radicals such as the n-octadecyl radical; cycloalkyl radicals such as the cyclopentyl, cyclohexyl or cycloheptyl radical and methylcyclohexyl radical; aryl radicals such as the phenyl, naphthyl, anthryl and phenanthryl radical; alkaryl radicals such as the o-, m- and p-tolyl, xylyl, mesitylenyl and o-, m- and p-ethylphenyl radical; and aralkyl radicals such as the benzyl radical, the α- and β-phenylethyl radical.

The radical ($R^{b-}H$) is a cyclopentadienyl anion, which consists of a singly negatively charged aromatic five-ring system $C_5R^x_5{}^-$, substituted by the radicals $R^x$.

The radicals $R^x$ in the compound of general formula III are preferably each independently hydrogen, linear or branched, acyclic or cyclic, saturated or mono- or polyunsaturated C1-C20 alkyl or C6-C20 aryl, particularly preferably C1-C3 alkyl, especially preferably methyl radicals.

At least one of the radicals $R^x$ is preferably a group —$CHR^1R^2$, wherein the radicals $R^1$ and $R^2$ are each independently hydrogen, linear or branched, acyclic or cyclic, saturated or mono- or polyunsaturated C1-C20 alkyl or C6-C20 aryl, particularly preferably C1-C3 alkyl, especially preferably methyl radicals. Examples of radicals $R^x$ are alkyl radicals such as the methyl, ethyl, n-propyl, isopropyl, n-butyl, sec-butyl, isobutyl, tert-butyl, n-pentyl, sec-pentyl, isopentyl, neopentyl or tert-pentyl radical; hexyl radicals such as the n-hexyl radical; heptyl radicals such as the n-heptyl radical; octyl radicals such as the n-octyl radical, and isooctyl radicals such as the 2,4,4-trimethylpentyl radical; nonyl radicals such as the n-nonyl radical; decyl radicals such as the n-decyl radical; dodecyl radicals such as the n-dodecyl radical; hexadecyl radicals such as the n-hexadecyl radical; octadecyl radicals such as the n-octadecyl radical; cycloalkyl radicals such as the cyclopentyl, cyclohexyl or cycloheptyl radical and methylcyclohexyl radical; aryl radicals such as the phenyl, naphthyl, anthryl and phenanthryl radical; alkaryl radicals such as the o-, m- and p-tolyl, xylyl, mesitylenyl and o-, m- and p-ethylphenyl radical; and aralkyl radicals such as the benzyl radical, the α- and β-phenylethyl radical.

Compounds A are hydride acceptors. Preferred compounds A are $MX_3$ where M=B, Al and Ga and $MX_5$ where M=P, As, Sb, Ir and Pt. The radicals X each independently have the definition of an optionally substituted saturated, unsaturated, acyclic or cylic optionally substituted carbon or carbonoxy radical or have the definition of halogen.

Particularly preferred radicals X in the compounds $MX_3$ are C1-C20 alkyl, C1-C20 alkoxy, C6-C20 aryl or C6-C20 aryloxy radicals, which are substituted by halogen, preferably fluorine, or fluorine, chlorine and bromine.

Particularly preferred radicals X in the compounds $MX_5$ are fluorine, chlorine and bromine.

Preferred examples of compounds A are:
$BF_3$, $BCl_3$, $AlF_3$, $AlCl_3$, $PCl_3$, $AsF_5$, $SbF_5$, $SbCl_5$, $PCl_5$, $PF_5$, $B(C_6F_5)_3$, $B(CF_3)_3$, $B(C_6Cl_5)_3$, $B(C_6H_5)_3$, $B(2,6$-difluoro-$C_6H_3)_3$, $B(2,4,6$-trifluoro-$C_6H_2)_3$, $B(2\text{-}C_6F_5\text{-}C_6F_4)_3$, $B(2,3,5,6$-tetrafluoro-$C_6H)_3$, $B(4,5,6,7$-tetrafluoro-2-naphthyl$)_3$, $Al(C_6F_5)_3$, $Ga(C_6F_5)_3$, $B[C_6H_2(CF_3)_3]_3$, $Al(OR^{PF})_3$, $FAl(OR^{PF})_2$ and $Sb(OTeF_5)_5$.

The compound $HA^-$ that is formed in the reaction according to reaction equation 1 forms the counterion to the cationic silicon (II) compound $(R^aSi)^+$.

However, it is also possible to exchange the anion $HA^-$ by other anions, for example by a resalting reaction which is downstream of the reaction according to the invention for example.

Also formed in the reaction is the cleavage product $R^b$, which has the definition $Cp=CR^1R^2$ according to exemplary reaction equation 1. Cleavage products $R^b$ may be left in the reaction mixture or can however be removed if this is advantageous, for example if $R^b$ interferes in catalytic processes.

The removal can be effected in a manner known to those skilled in the art, for example by distillation or by fractional crystallization. The compound $R^b$ is preferably distilled off in the distillative process, preferably under reduced pressure. If the removal is effected by crystallization, the compound of general formula I thus is preferably crystallized out by adding a precipitating agent and can be filtered off for example, the compound of general formula $R^b$ remaining in solution.

The molar ratio of the compound of general formula II and the hydride acceptor A is preferably at least 1:10 and at most 10:1, particularly preferably at least 1:5 and at most 5:1, especially preferably at least 1:3 and at most 3:1. The two components can be mixed in any sequence here, wherein the mixing is carried out in a manner known to those skilled in the art.

The reaction according to the invention can be carried out in the presence of one or more further components, for example, in the presence of one solvent or a mixture of two or more solvents.

Either the compound of general formula II or the compound A or both components can be dissolved in one solvent or in a solvent mixture. The proportion of solvent or solvent mixture, based on the sum of the compounds of general formula II and A, is preferably at least 0.1% by weight and at most 1000-fold the amount by weight, particularly preferably at least 10% by weight and at most 100-fold the amount by weight, especially preferably at least 30% by weight and at most 10-fold the amount by weight.

The solvents used can be, for example, hydrocarbons such as pentane, hexane, heptane, cyclohexane or toluene, chlorohydrocarbons such as dichloromethane, chloroform, chlorobenzene or 1,2-dichloroethane, ethers such as diethyl ether, methyl tert-butyl ether, anisole, tetrahydrofuran or dioxane, or nitriles such as acetonitrile or propionitrile.

The reaction according to the invention to give the compound of general formula I may also be carried out in the presence of components which react in the presence of the compound of general formula I. The compound of general formula I effective as catalyst for the reaction of the further components is in this case generated in the presence of the reactants.

The reaction can be carried out at atmospheric pressure or under reduced pressure or under elevated pressure.

The pressure is preferably at least 0.01 bar and at most 100 bar, particularly preferably at least 0.1 bar and at most 10 bar, the reaction being carried out especially preferably at atmospheric pressure.

The reaction according to the invention is preferably carried out at temperatures between at least −100° C. and at most +250° C., particularly preferably between at least −20°

C. and at most +150° C., especially preferably between at least 0° C. and at most +100° C.

The invention further relates to the cationic Si(II) compounds of general formula I $$(R^a Si)^+ HA^- \qquad (I).$$

Examples of compounds of general formula I are: $(C_5Me_5)Si^+HB(C_6F_5)_3^-$, $(C_5Me_5)Si^+HBF_3^-$, $(C_5Me_5)Si^+HB(CF_3)_3^-$, $(C_5Me_5)Si^+HB(C_6Cl_5)_3^-$, $(C_5Me_5)Si^+HB(C_6H_5)_3^-$, $(C_5Me_5)Si^+HB(2,6\text{-difluoro-}C_6H_3)_3^-$, $(C_5Me_5)Si^+HB(2,4,6\text{-trifluoro-}C_6H_2)_3^-$, $(C_5Me_5)Si^+HB(2\text{-}C_6F_5\text{-}C_6F_4)_3^-$, $(C_5Me_5)Si^+HB(2,3,5,6\text{-tetrafluoro-}C_6H)_3^-$, $(C_5Me_5)Si^+HB(4,5,6,7\text{-tetrafluoro-2-naphthyl})_3^-$, $(C_5Me_5)Si^+HB[C_6H_2(CF_3)_3]_3^-$, $(C_5Me_5)Si^+HAl(C_6F_5)_3^-$, $(C_5Me_5)Si^+HGa(C_6F_5)_3^-$, $(C_5Me_5)Si^+Al(OR^{PF})_3^-$, $(C_5Me_5)Si^+HFAl(OR^{PF})_2^-$, $(C_5Me_5)Si^+Sb(OTeF_5)_5^-$, $(C_5Me_5)Si^+HBCl_3^-$, $(C_5Me_5)Si^+HAlF_3^-$, $(C_5Me_5)Si^+HAlCl_3^-$, $(C_5Me_5)Si^+HPCl_3^-$, $(C_5Me_5)Si^+HAsF_5^-$, $(C_5Me_5)Si^+HSbF_5^-$, $(C_5Me_5)Si^+HSbCl_5^-$, $(C_5Me_5)Si^+HPCl_5^-$, $(C_5Me_5)Si^+HPF_5^-$, $(C_5iPr_5)Si^+HB(C_5F_5)_3^-$ and $(C_5iPr_5)Si^+HBF_3^-$, $(C_5H_2Me_3)Si^+HB(C_6F_5)_3^-$, $(C_5H_2Me_3)Si^+HBF_3^-$.

The cationic silicon (II) compounds of general formula I can be used as catalysts, for example for conversion reactions of ethers, cationic polymerizations and hydrosilylations. As could be shown as in the example of hydrosilylation, processes that are catalysed by silicon (II) compounds of general formula I proceed particularly uniformly and without notable formation of by-products.

All aforementioned symbols of the formulae above are each defined independently of one another. In all formulae, the silicon atom is tetravalent.

Unless stated otherwise in each case, all amounts and percentages are based on weight and all temperatures are 20° C.

EXAMPLES

The reaction of silicocene, $(C_5Me_5)_2Si$ with the hydride acceptor $B(C_6F_5)_3$ at 20° C. affords in quantitative yield the cationic silicon (II) compound $(C_5Me_5)Si^+HB(C_6F_5)_3^-$ and tetramethylfulvene $(C_5Me_4)=CH_2$.

Example 1

All process steps are carried out under Ar. 20.1 mg (0.067 mmol) of decamethylsilicocene [$(C_5Me_5)_2Si$, formula II where $R^a=C_5Me_5$ and $(R^{b-}H)=C_5Me_5^-$], and 30.0 mg (0.059 mmol) of tris(pentafluorophenyl)borane are each dissolved in 0.5 ml of $CD_2Cl_2$ and the solutions combined in an NMR tube. A dark yellow coloration is immediately formed which indicates the formation of tetramethylfulvene. The solution comprises the compound $(Me_5C_5)Si^+BH(C_6F_5)_3^-$.

The signals of this compound remain unchanged at 20° C. over a time period of 35 days, i.e. no conversion degradation takes place.

$^1$H-NMR ($CD_2Cl_2$): δ=1.83 and 1.88 (2s, 4 Me of tetramethylfulvene), 2.19 [s, $(C_5Me_5)Si^+$], 3.57 [q, broad, J(HB)= 17 Hz, H—B($C_6F_5)_3^-$], 5.40 (s, 2H, $H_2C$= of tetramethylfulvene); $^{19}$F-NMR ($CD_2Cl_2$): δ=−133.6 (m, 2F); −164.1 (m, 1F); −167.2 (m, 2F);

$^{29}$Si—NMR ($CD_2Cl_2$): δ=−399.1.

Example 2

All process steps are carried out under Ar. 11.8 mg (0.046 mmol) of decamethylsilicocene [$(C_5Me_5)_2Si$] and 23.3 g (0.046 mmol) of tris(pentafluorophenyl)borane are weighed successively into an NMR tube and 1 ml of $CDCl_3$ is added. The two components dissolve and a dark yellow coloration is immediately formed which indicates the formation of tetramethylfulvene. The solution comprises the compound $(Me_5C_5)Si^+BH(C_6F_5)_3^-$.

$^1$H-NMR ($CDCl_3$): δ=1.76 and 1.82 (2s, 4 Me of tetramethylfulvene), 2.10 [s, $(C_5Me_5)Si^+$], 3.48 [q, broad, H—B($C_6F_5)_3^-$], 5.40 (s, 2H, $H_2C$=);

$^{29}$Si-NMR ($CDCl_3$): δ=−399.9.

Example 3

All process steps are carried out under Ar. 100 mg (0.335 mmol) of decamethylsilicocene and 172 mg (0.335 mmol) of tris(pentafluorophenyl)borane are each dissolved in 0.5 ml of $CD_2Cl_2$ and the two solutions are combined. The solution immediately colors dark yellow, the reason being the formation of tetramethylfulvene. Heptane is added, whereupon a colorless crystalline precipitate of the compound $(Me_5C_5)Si^+BH(C_6F_5)_3^-$ is formed. The suspension is concentrated a little under reduced pressure to remove $CD_2Cl_2$ and 1 ml of heptane is again added.

The solution is removed using a syringe and the crystalline residue is washed twice more with 1 ml of heptane each time. It is dried at 20° C. under high vacuum and 155 mg (64%) of the pure fulvene-free product $(Me_5C_5)Si^+BH(C_6F_5)_3^-$ is obtained.

Example 4

Hydrosilylation Reaction

All process steps are carried out under Ar. 118.5 mg (1.00 mmol) of α-methylstyrene and 136.7 mg (1.00 mmol) of dimethylphenylsilane are dissolved in 0.5 ml of $CD_2Cl_2$ and, at 20° C., a solution of 2.8 mg (0.0041 mmol) of the compound $(Me_5C_5)Si^+BH(C_6F_5)_3^-$ (prepared as in example 3) in 0.5 ml of $CD_2Cl_2$ is added. The hydrosilylation reaction that occurs spontaneously with formation of the product $PhSiMe_2$—$CH_2$—$CH(CH_3)$ Ph is monitored by $^1$H-NMR spectroscopy. After 20 minutes ca. 50% product has formed and the reaction is complete after 24 hours.

Example 5

Hydrosilylation Reaction

All process steps are carried out under Ar. To the NMR sample prepared according to example 1, comprising the compound $(Me_5C_5)Si^+BH(C_6F_5)_3^-$ and tetramethylfulvene, is added 9.1 mg (0.067 mmol) of dimethylphenylsilane. The initially still dark yellow solution decolorizes within a few hours. The yellow-colored tetramethylfulvene reacts completely with dimethylphenylsilane to form the hydrosilylation product $PhSiMe_2$—$CH_2$—$C_5Me_4$ (NMR spectroscopic investigation). The compound $(Me_5C_5)Si^+BH(C_6F_5)_3^-$ is verified in unchanged amount by $^1$H-NMR spectroscopy (singlet at δ=2.2 ppm).

Example 6

Hydrosilylation Reaction

All process steps are carried out under Ar. To a solution in $CD_2Cl_2$ prepared according to example 1, comprising 0.033 mmol of the compound $(Me_5C_5)Si^+BH(C_6F_5)_3^-$ and tetramethylfulvene respectively, is added a mixture of 17.4 mg (0.147 mmol) of α-methylstyrene and 14.3 mg (0.105 mmol) of dimethylphenylsilane. The products of the hydrosilylation reactions of dimethylphenylsilane with α-methylstyrene [PhSiMe$_2$-CH$_2$—CH(CH$_3$)Ph] and with tetramethylfulvene (PhSiMe$_2$-CH$_2$-C$_5$Me$_4$) are formed.

The invention claimed is:

1. A method for producing cationic silicon (II) compounds of general formula I, comprising:

$$(R^aSi)^+HA^- \quad (I)$$

reacting the silicon (II) compounds of general formula II $$(R^{b-}H)(R^aSi)^+ \quad (II)$$

with a compound A,
where
R$^a$ is a carbon-containing radical, which may additionally comprise heteroatoms, bound to the cationic silicon atom via a covalent bond, ionic bond or via one or more π bonds with the cationic silicon atom,
(R$^{b-}$H) is a p-bonded singly negatively charged radical of general formula III,

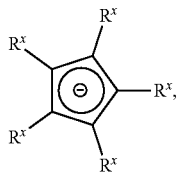

(III)

R$^x$ are monovalent or polyvalent organic radicals, which may also be bonded to one another to form a fused ring, with the proviso that at least one of the radicals R$^x$ is an organic radical bonded via carbon bearing at least one hydrogen atom, and
A is a compound which, as an electrophile, is capable of accepting electron pairs, wherein said compound has formula MX$_3$ where M is=B, Al or Ga, and where X is a C6-C20 aryl radical substituted by halogen.

2. The method of claim 1, wherein the radicals R$^x$ are each independently hydrogen, linear or branched, acyclic or cyclic, saturated or mono- or polyunsaturated C1-C20 alkyl or C6-C20 aryl radicals.

3. The method of claim 1, wherein R$^a$ is a p-bonded cyclopentadienyl radical substituted by the radicals R$^y$(R$^y_5$Cp) wherein
R$^y$ are monovalent or polyvalent organic radicals, which may be bonded to one another to also form fused rings.

4. The method of claim 1, wherein said reacting the silicon (II) compounds of general formula II with the compound A is carried out in aprotic solvents selected from the group consisting of hydrocarbons, chlorohydrocarbons, ethers, nitriles, organosilanes and organosiloxanes.

5. A cationic silicon (II) compound of general formula I $$(R^aSi)^+HA^- \quad (I)$$

where
R$^a$ is a carbon-containing radical, which may additionally comprise heteroatoms, bound to the cationic silicon atom via a covalent bond, ionic bond or via one or more p bonds with the cationic silicon atom and
A is a compound which, as an electrophile, is capable of accepting electron pairs, having formula MX$_3$ where M is=B, Al or Ga, and where X is a C6-C20 aryl radical substituted by halogen.

6. The cationic silicon (II) compounds of general formula 1as claimed in claim 5, wherein said cationic silicon (II) compounds are catalysts.

* * * * *